(12) United States Patent
Sasing et al.

(10) Patent No.: US 9,861,486 B2
(45) Date of Patent: Jan. 9, 2018

(54) INSTRUMENTS AND METHODS FOR LOCATING A FEMORAL MECHANICAL AXIS

(71) Applicant: Orthopaedic International, Inc., Cabuyao, Laguna (PH)

(72) Inventors: Jude L. Sasing, Quezon (PH); Ramon B. Gustilo, Eden Prairie, MN (US)

(73) Assignee: Orthopaedic International, Inc., Cabuyao, Labuna (PH)

( * ) Notice: Subject to any disclaimer, the term of this patent is extended or adjusted under 35 U.S.C. 154(b) by 641 days.

(21) Appl. No.: 14/175,228

(22) Filed: Feb. 7, 2014

(65) Prior Publication Data

US 2014/0228852 A1    Aug. 14, 2014

Related U.S. Application Data

(60) Provisional application No. 61/762,492, filed on Feb. 8, 2013, provisional application No. 61/904,083, filed
(Continued)

(51) Int. Cl.
*A61B 17/17* (2006.01)
*A61F 2/38* (2006.01)
(Continued)

(52) U.S. Cl.
CPC .......... *A61F 2/3859* (2013.01); *A61B 17/155* (2013.01); *A61B 17/157* (2013.01); *A61B 17/1764* (2013.01); *A61F 2/389* (2013.01); *A61F 2/3877* (2013.01); *A61F 2/4657* (2013.01); *A61F 2/38* (2013.01); *A61F 2002/4668* (2013.01)

(58) Field of Classification Search
CPC ............ A61F 2002/4668; A61F 2/4657; A61F 2002/4658
See application file for complete search history.

(56) References Cited

U.S. PATENT DOCUMENTS 5,330,534 A    7/1994   Herrington et al.
5,358,527 A    10/1994  Forte
(Continued)

FOREIGN PATENT DOCUMENTS

EP    0 677 274    1/2003
EP    2 083 714    12/2011

OTHER PUBLICATIONS

Zimmer MIS Multi-Reference 4-in-1 Femoral Instrumentation Surgical Technique, Copyright 2009 Zimmer Inc.

*Primary Examiner* — David Bates
(74) *Attorney, Agent, or Firm* — Kagan Binder, PLLC

(57) ABSTRACT

An instrument for locating a femoral mechanical axis and identifying the locations of at least three points in space in relation to the center of a femoral head, the instrument including a base member, an extension arm clamp translationally and pivotally attached to the base member, an extension arm translationally and pivotally attached to the extension arm clamp, a swiveling arm pivotally attached to a distal end of the extension arm, the swiveling arm including a lateral locator member at a proximal end and a medial locator member at a distal end, a bracket pivotally attached to the swiveling arm, and a locating arm removably attached to the bracket, the locating arm including a middle locator member.

17 Claims, 15 Drawing Sheets

Related U.S. Application Data on Nov. 14, 2013, provisional application No. 61/904,086, filed on Nov. 14, 2013, provisional application No. 61/904,099, filed on Nov. 14, 2013.

(51) Int. Cl.
*A61B 17/15* (2006.01)
*A61F 2/46* (2006.01)

(56) References Cited

U.S. PATENT DOCUMENTS

| | | |
|---|---|---|
| 5,520,694 A | 5/1996 | Dance et al. |
| 5,601,566 A | 2/1997 | Dance et al. |
| 5,611,353 A | 3/1997 | Dance et al. |
| 5,690,638 A | 11/1997 | Dance et al. |
| 5,871,540 A | 2/1999 | Weissman et al. |
| 6,478,799 B1 | 11/2002 | Williamson |
| 6,928,742 B2 | 8/2005 | Broers et al. |
| 7,331,932 B2 | 2/2008 | Leitner |
| 7,427,272 B2 | 9/2008 | Richard et al. |
| 7,708,740 B1 | 5/2010 | Bonutti |
| 7,805,852 B2 | 10/2010 | Collette |
| 7,875,081 B2 | 1/2011 | Lipman et al. |
| 7,892,240 B2 | 2/2011 | Claypool et al. |
| 7,967,822 B2 | 6/2011 | Haines et al. |
| 8,092,546 B2 | 1/2012 | Coon et al. |
| 8,118,811 B2 | 2/2012 | Coon et al. |
| 8,172,842 B2 | 5/2012 | Sasing |
| 8,308,730 B2 | 11/2012 | Radermacher et al. |
| 8,409,210 B2 | 4/2013 | Bhatnagar et al. |
| 2005/0070897 A1 | 3/2005 | Petersen |
| 2006/0184173 A1 | 8/2006 | Collazo |
| 2009/0088754 A1 | 4/2009 | Aker et al. |
| 2009/0125029 A1 | 5/2009 | Seo et al. |
| 2009/0216247 A1* | 8/2009 | Collette ............... A61B 17/155 606/130 |
| 2009/0228111 A1 | 9/2009 | Otto |
| 2010/0191298 A1 | 7/2010 | Earl et al. |
| 2011/0144704 A1 | 6/2011 | Switzer |
| 2011/0305379 A1 | 12/2011 | Mahfouz |
| 2012/0029581 A1 | 2/2012 | Kanekasu |
| 2012/0232671 A1 | 9/2012 | Bojarski et al. |

\* cited by examiner

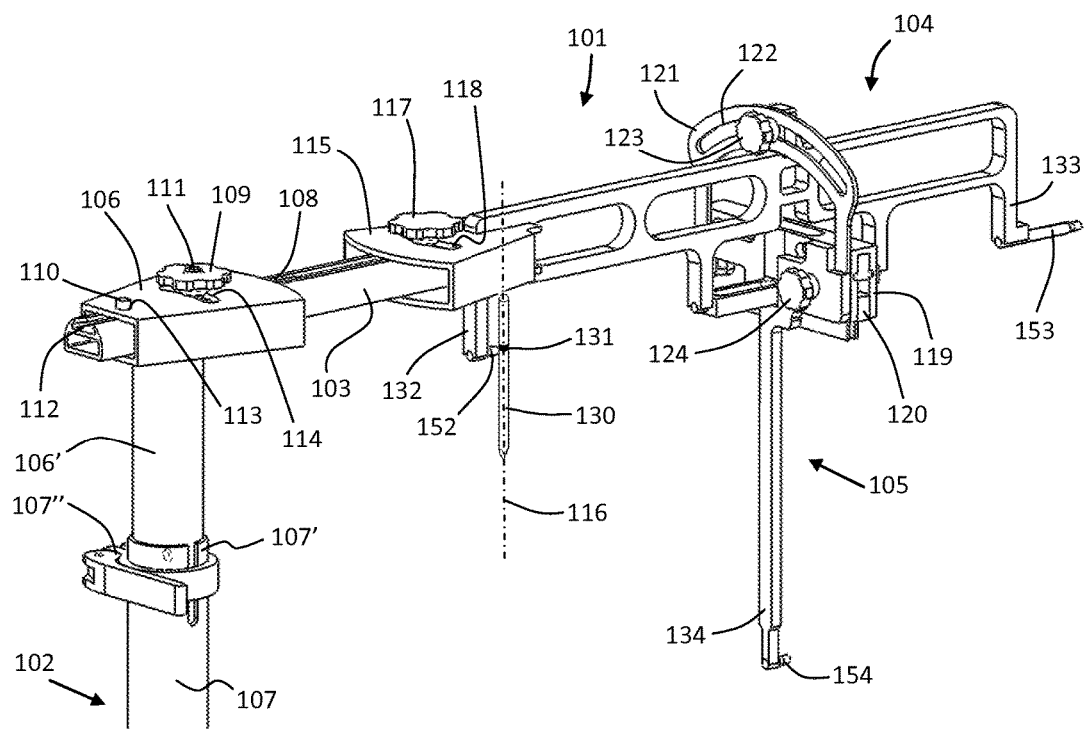
Figure 18
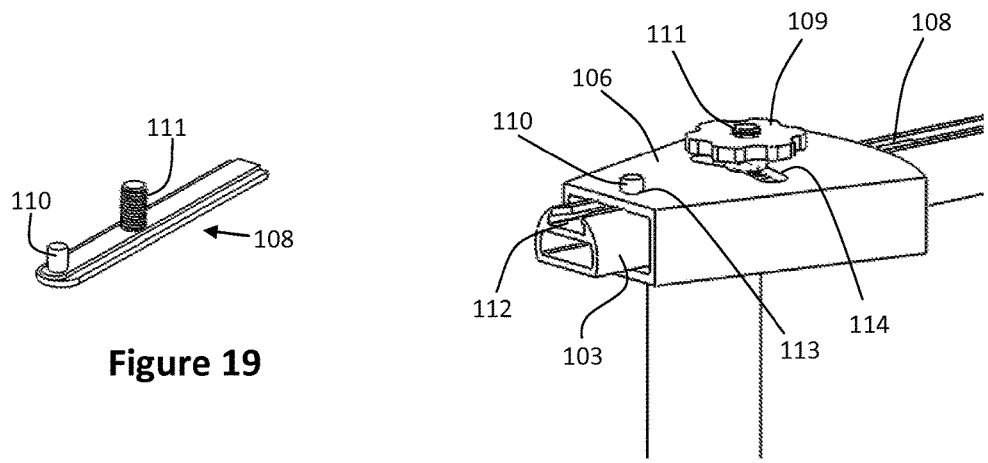
Figure 19
Figure 20

INSTRUMENTS AND METHODS FOR LOCATING A FEMORAL MECHANICAL AXIS

CROSS-REFERENCE TO RELATED APPLICATIONS

This application claims the benefit of U.S. Provisional Patent Application No. 61/762,492, filed Feb. 8, 2013 entitled "INSTRUMENT FOR LOCATING THE FEMORAL MECHANICAL AXIS", U.S. Provisional Patent Application No. 61/904,083, filed Nov. 14, 2013 entitled "INSTRUMENTS AND METHODS FOR LOCATING A FEMORAL MECHANICAL AXIS", U.S. Provisional Patent Application No. 61/904,086, filed Nov. 14, 2013 entitled "TOTAL KNEE ARTHROPLASTY METHODS, SYSTEMS, AND INSTRUMENTS", and U.S. Provisional Patent Application No. 61/904,099, filed Nov. 14, 2013 entitled "TOTAL KNEE ARTHROPLASTY METHODS, SYSTEMS, AND INSTRUMENTS", which applications are incorporated herein by reference in their entireties.

TECHNICAL FIELD

The present invention relates to locating the mechanical axis of a femur, which is generally defined as the line connecting the center of the femoral head and the center of the knee joint. In particular, the invention is used to locate the mechanical axis during total knee arthroplasty.

BACKGROUND

The successful outcome of a total knee arthroplasty relies on accurate bone cuts and adequate ligament balancing. In order for the knee implants to function properly, accurate bone cuts must be made in relation to the mechanical axis of the femur. Furthermore, the lateral and/or medial collateral ligaments must be released so the tibial mechanical axis aligns with the femoral mechanical axis. The tibial mechanical axis is relatively easy to identify because it is the same as the tibial anatomical axis. On the other hand, the femoral mechanical axis is more difficult to identify because it extends from the center of the femoral head to the center of the knee joint, but the femoral head cannot be visualized during total knee surgery. In general, the femoral mechanical axis is oriented approximately 6 degrees medial to the femoral anatomical axis, but this orientation varies with anatomical variations among patients.

The most widely used method of locating the mechanical axis is with a rod that is positioned in the femoral medullary canal. The mechanical axis is then estimated to be positioned approximately 6 degrees medially from the axis of the rod. Although this method can be easy to implement, it is not very accurate due to variations in the anatomy of the femur and due to the play between the rod and the medullary canal in which it is positioned. This method also cannot determine the direction of the mechanical axis when viewed in the sagittal plane. Furthermore, this method requires the medullary canal to be violated, which can potentially lead to more blood loss and possible complications. Another way of locating the mechanical axis is by using computerized navigation equipment to identify bony landmarks and relate them to the motion of the femur to locate the mechanical axis. However, such equipment is very expensive, and can be cumbersome to use in surgery. Thus, there is a need to provide systems and methods that do not require the use of computerized navigation equipment to locate the femoral mechanical axis accurately in both the coronal and sagittal planes.

SUMMARY

The invention described herein relates to locating the center of the femoral head of a patient, which information is in turn used to locate the mechanical axis of the femur in both the coronal and sagittal planes. That is, instruments and methods described herein are useful for locating the femoral mechanical axis in three dimensions.

In accordance with an aspect of the invention, an instrument is provided for locating a femoral mechanical axis and identifying the locations of at least three points in space in relation to the center of a femoral head. The instrument comprises a base member, an extension arm clamp translationally and pivotally attached to the base member, an extension arm translationally and pivotally attached to the extension arm clamp, a swiveling arm pivotally attached to a distal end of the extension arm, the swiveling arm comprising a lateral locator member at a proximal end and a medial locator member at a distal end, a bracket pivotally attached to the swiveling arm, and a locating arm removably attached to the bracket, the locating arm comprising a middle locator member.

In accordance with another aspect of the invention, a method is provided for locating a femoral mechanical axis. The method comprises the steps of identifying a representative sphere traced by a trace point offset by a predetermined distance from a center of a knee, wherein a center of the representative sphere is coincident with a center of a femoral head, identifying three points on the representative sphere, locating the center of a circle defined by the three points on the representative sphere, identifying a line passing through the center of, and perpendicular to the plane of, the circle defined by the three points on the representative sphere, positioning the femur such that a line connecting the center of the femoral head and the trace point is coincident with the line passing through the center of, and perpendicular to the plane of, the circle defined by the three points on the representative sphere, and placing a plurality of locating devices on the femur to identify the location of the femoral mechanical axis in both the coronal and sagittal planes. Such locating devices are positioned on the femur in a way that compensates for the predetermined offset of the trace point from the center of the knee so that the line connecting the center of the femoral head and the trace point has a predetermined angular offset from the femoral mechanical axis.

BRIEF DESCRIPTION OF THE DRAWINGS

The present invention will be further explained with reference to the appended Figures, wherein like structure is referred to by like numerals throughout the several views, and wherein:

FIG. 18 is a perspective view of an embodiment of a mechanical axis finder of the invention;

FIG. 19 is an enlarged perspective view of a sliding member of the mechanical axis finder of FIG. 18;

FIG. 20 is an enlarged perspective view of a portion of the mechanical axis finder of FIG. 18;

DETAILED DESCRIPTION

Figure 1:
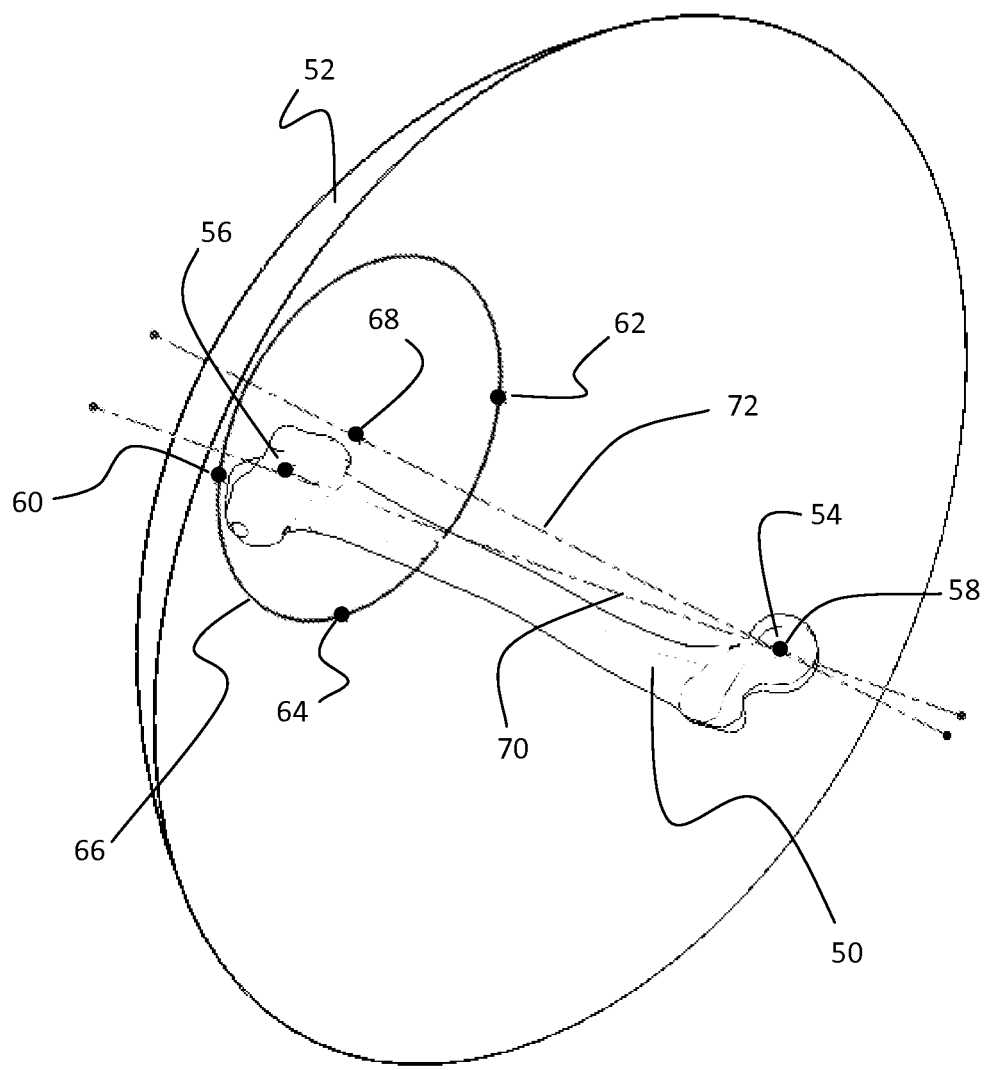
FIG. 1 is a schematic diagram of a representative sphere in relation to a femur.

Referring now to the Figures, wherein the components are labeled with like numerals throughout the several Figures, and initially to FIG. 1, a schematic diagram of a femur 50 and a portion of a sphere 52 is shown. The sphere 52 and the femur 50 are positioned so that the center of the femoral head 54 coincides with the center 58 of sphere 52. Furthermore, the center of the knee 56 is on the surface of the sphere 52. Thus, sphere 52 has a radius equal to the distance from the center of the femoral head 54 to the center of the knee 56.

In accordance with the present invention, issues that are commonly encountered when attempting to locate the mechanical axis of a femur can be solved by finding a line that passes through the center 58 of sphere 52 using points on the surface of the sphere, such as first point 60, second point 62, and third point 64, as are shown in FIG. 1. Locating such a line can be accomplished using devices and/or methods of the present invention. Further in accordance with the invention, the physical movement of a knee is presumed to pivot three-dimensionally around the center of the femoral head. Thus, the center of the knee 56 will trace the surface of sphere 52 when the knee is moved about, whereby it moves through points 60, 62, and 64.

It can be shown that for any given sphere, a line passing through the center of, and perpendicular to the plane of, a circle defined by at least three points on the sphere will pass through the center of the sphere. As applied to the present invention, points 60, 62, and 64 of FIG. 1 are on the surface of sphere 52 and are used to define a circle 66 with center 68. In order to locate the mechanical axis 70 for a particular femur, the center of the knee 56 is moved to an arbitrary point in space that can be made to correspond to first point 60. The center of the knee 56 is then moved to second point 62, and finally to third point 64. These points 60, 62, and 64 are used to define circle 66, and then point 68 can then be identified as the center of this circle. After all of these points are identified and/or located, the axis 72 can be identified, which is perpendicular to the plane containing circle 66 and passing through the center 68 of circle 66. By moving the center of the knee 56 to coincide with axis 72, the mechanical axis 70 of the femur 50 becomes collinear with an axis 72, allowing it to be located. Devices and methods of the invention are used to identify points 60, 62, 64, and 68, and axis 72 in relation to a femur, and are used to locate the femoral mechanical axis, are described in the succeeding paragraphs.

Figure 2:
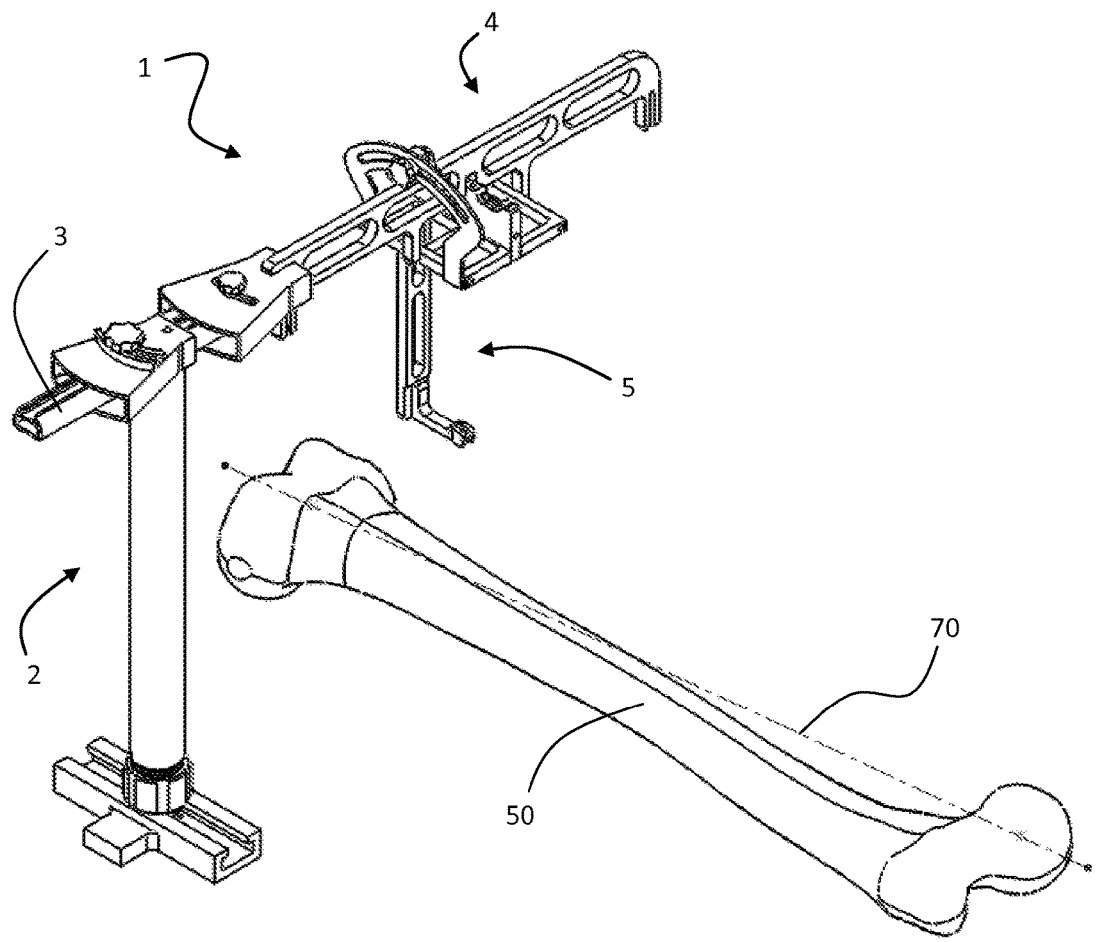
FIG. 2 is a perspective view of an embodiment of a mechanical axis finder of the invention positioned relative to a femur.

Referring now to FIG. 2, an embodiment of a mechanical axis finder 1 of the invention is illustrated, which generally includes a base 2, an extension arm 3, a swiveling arm 4, and a locating arm 5. A representative or exemplary femur 50 of a patient is also shown adjacent to the mechanical axis finder 1. Base 2 is attachable to an operating table by clamping it to the side rail of the table or by using any other attachment structure or structures that provide for secure engagement between the mechanical axis finder and the table.

Figure 3:
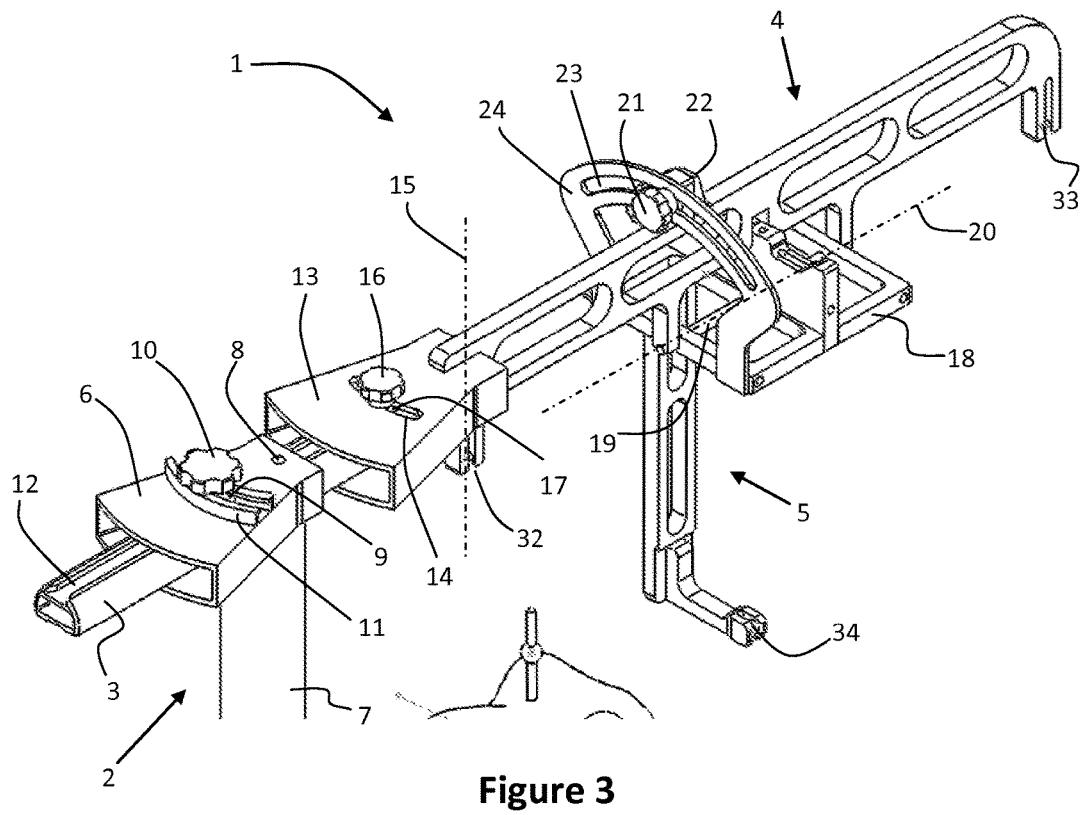
FIG. 3 is a detailed perspective view of the mechanical axis finder of FIG. 2.

FIG. 3 shows an enlarged view of a portion of mechanical axis finder 1 of FIG. 2. As shown, base 2 includes an extension arm clamp 6 on top of a post 7. In general, clamp 6 includes a base or structure that includes a flared or angled opening designed such that it allows extension arm 3 to translate and rotate relative to post 7 when in an unlocked configuration. When clamp 6 is in a locked configuration, however, as is discussed below, extension arm 3 is not translatable or rotatable relative to base 2.

With continued reference to the embodiment of FIG. 3, extension arm clamp 6 includes a pivot peg or member 8, a sliding nut 9, and a locking screw 10. Locking screw 10 is threaded for engagement with corresponding threads of sliding nut 9. Sliding nut 9 is positioned for sliding within or along curved slideway 11. In addition, extension arm 3 includes a longitudinally extending slot 12, and pivot peg 8 is engageable with the slot 12 for translation and rotation between the components. In this way, when clamp 6 is in an unlocked configuration, extension arm 3 is translatable relative to clamp 6 (via slot 12) and is rotatable at the same time about pivot peg 8. It is further noted that the locking screw 10 is engaged with slot 12 so that it remains coupled to extension arm 3 regardless of the orientation of extension arm 3 relative to clamp 6. The components of clamp 6 are therefore moveable to their desired locations relative to each other when in the unlocked configuration, and then the locking screw 10 can be tightened, such as by turning the locking screw 10, until it locks extension arm 3 to base 2. In this way, the extension arm 3 will be fixed translationally and rotationally relative to base 2. In another embodiment of the invention, clamp 6 may include features for being adjusted and locked vertically along the height of the post 7 to accommodate different heights of the anterior aspect of the femur from the operating table. In yet another embodiment, a different locking mechanism other than a locking screw can be used to secure the components to each other after their relative locations are adjusted.

Extension arm 3 is also connected to pivoting clamp 13 of swiveling arm 4 through a pin (not visible in the figures) that allows swiveling arm 4 to rotate about the axis 15 of the pin relative to extension arm 3. A locking screw 16 is threaded into a matching threaded hole 17 in extension arm 3 through a curved slot 14 in pivoting clamp 13. When in an unlocked configuration, the extension arm 3 and swiveling arm 4 will be moveable relative to each other, and then when the locking screw 16 is tightened, it locks swiveling arm 4 to extension arm 3. Again, it is contemplated that a mechanism other than a locking screw is used for locking the swiveling arm to the extension arm.

A bracket 18 is connected to the swiveling arm 4 via a pivot pin 19, thereby allowing bracket 18 to rotate relative to swiveling arm 4 about an axis 20 of pivot pin 19 when the components are in an unlocked configuration. An arch 24 extends upwardly from one side of bracket 18, which arch 24 includes a curved slot 23. A locking screw 21 or other mechanism is threaded into a threaded hole 22 of swiveling arm 4, and is slidable along curved slot 23 of arch 24. When locking screw 21 is tightened, it locks the bracket 18 in place relative to swiveling arm 4.

Figure 4:
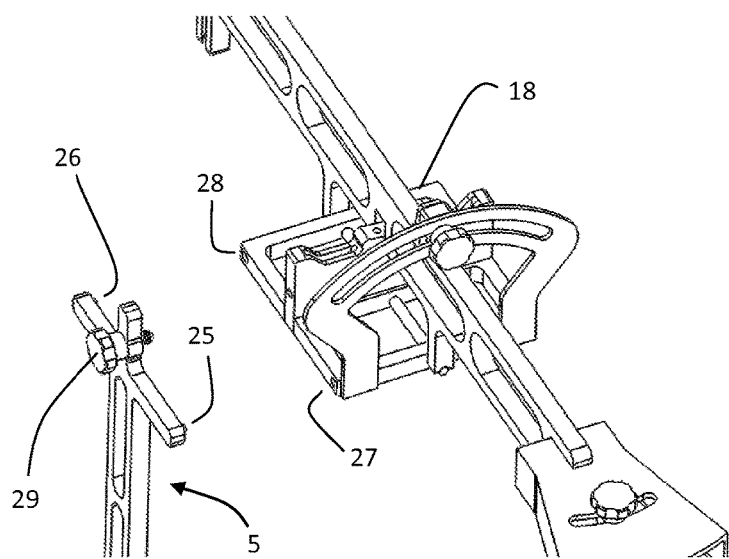
FIG. 4 is an exploded perspective view of a portion of the mechanical axis finder of FIG. 2.

With additional reference to FIG. 4, an exploded view of a portion of mechanical axis finder 1 is shown with the locating arm 5 detached from the bracket 18. Locating arm 5 includes two locating pegs 25 and 26 that engage hole 27 and slot 28 of bracket 18, respectively. A locking screw 29 or other mechanism is used for securing locating arm 5 to bracket 18.

Figure 5:
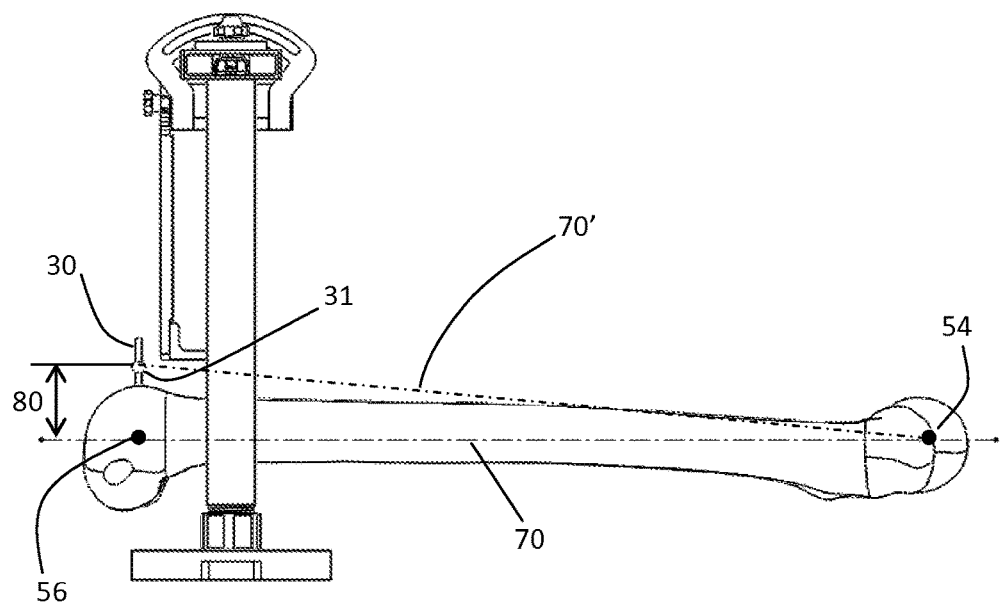
FIG. 5 is a side view of the mechanical axis finder of FIG. 2 positioned relative to a femur.
Figure 26:
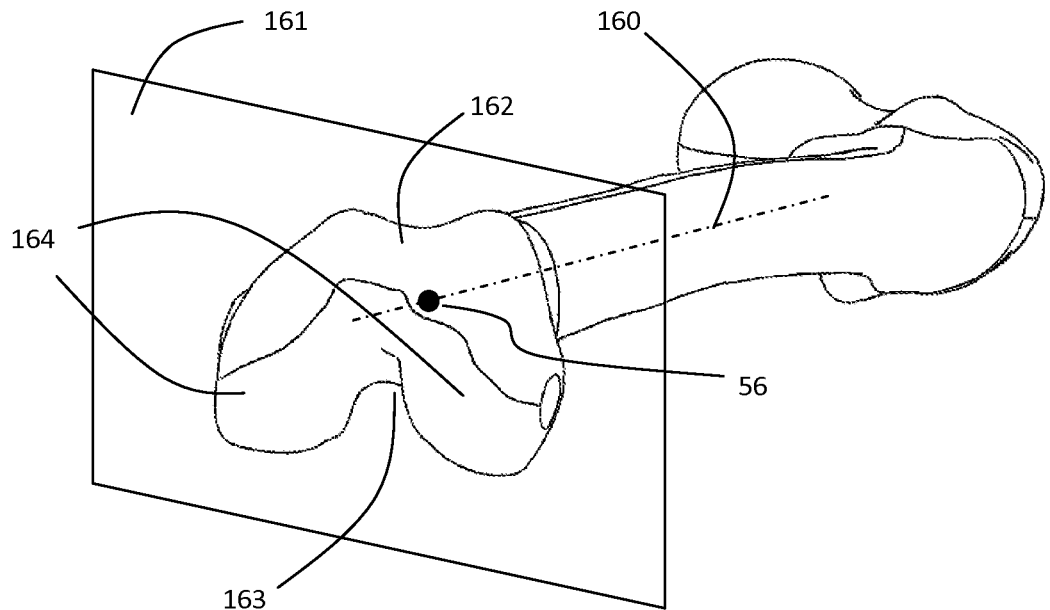
FIG. 26 is a perspective view of an anatomical plane located relative to a femur.

In an exemplary method of using a mechanical axis finder of the invention, an incision is first made to expose the knee joint of a patient. After the knee joint is exposed, the center of the knee is identified by the surgeon in the coronal and sagittal planes, wherein an exemplary center of the knee 56 is illustrated in FIG. 5. It should be noted that the sagittal plane being referred to in this and other paragraphs herein is a plane parallel to the anatomical sagittal plane and passing through the center of the knee. With reference to FIG. 26, the center of the knee 56 can be defined as a point along a line 160 perpendicular to a transverse anatomical plane 161, wherein the line passes through a point halfway between the deepest part of anterior aspect of the trochlear groove 162 and the deepest part of the intercondylar notch 163 when viewed from the distal end of the knee, and approximately 20 mm to 50 mm proximal from the distal surface of the femoral condyles 164.

Figure 27:
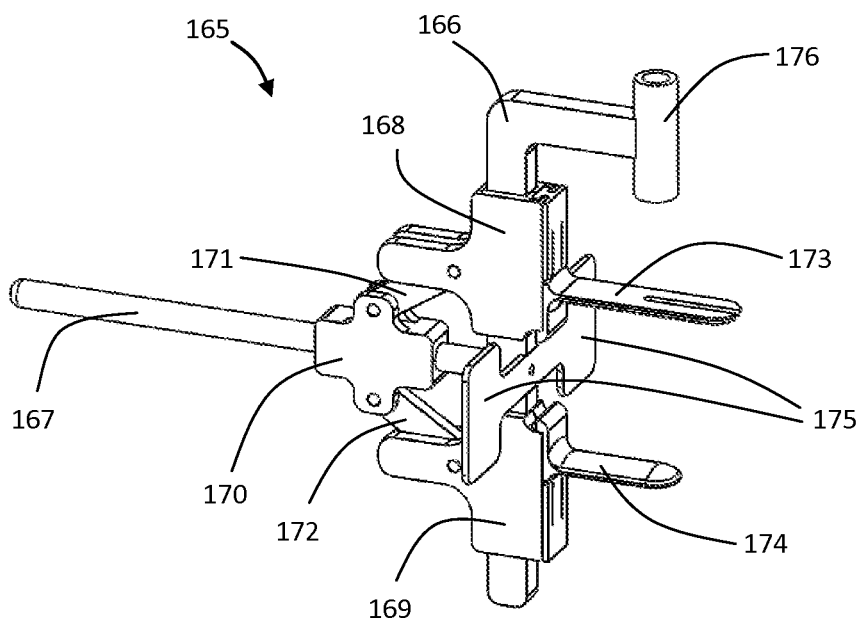
FIG. 27 is a perspective view of a knee center locator.

FIG. 27 shows an exemplary device or knee center locator 165 that can be used for locating the center of the knee 56, although it is understood that other devices or instruments can additionally or alternatively be used to accomplish the same purpose. Knee center locator 165 is composed of an anterior-posterior or AP guide bar 166, a proximal-distal or PD guide bar 167, anterior-posterior or AP guide sleeves 168 and 169, a proximal-distal or PD guide sleeve 170, connecting bars 171 and 172, an anterior locating jaw 173, a posterior locating jaw 174, locating paddles 175, and a pin guide 176. Anterior locating jaw 173 and posterior locating jaw 174 are removably connected to AP guide sleeves 168 and 169, respectively, so that different sizes of locating jaws can be used depending on the size of the knee. AP guide sleeves 168 and 169 can slide along AP guide bar 166 while PD guide sleeve 170 can slide along PD guide bar 167. AP guide sleeves 168 and 169 and PD guide sleeve 170 are pin-connected through connecting bars 171 and 172. Connecting bars 171 and 172 have approximately the same lengths so that the distance between PD guide bar 167 and anterior locating jaw 173 and the distance between PD guide bar 167 and posterior locating jaw 174 are approximately equal. Thus, PD guide bar 167 is located midway between anterior locating jaw 173 and posterior locating jaw 17, regardless of the distance between anterior locating jaw 173 and posterior locating jaw 174.

Figure 28:
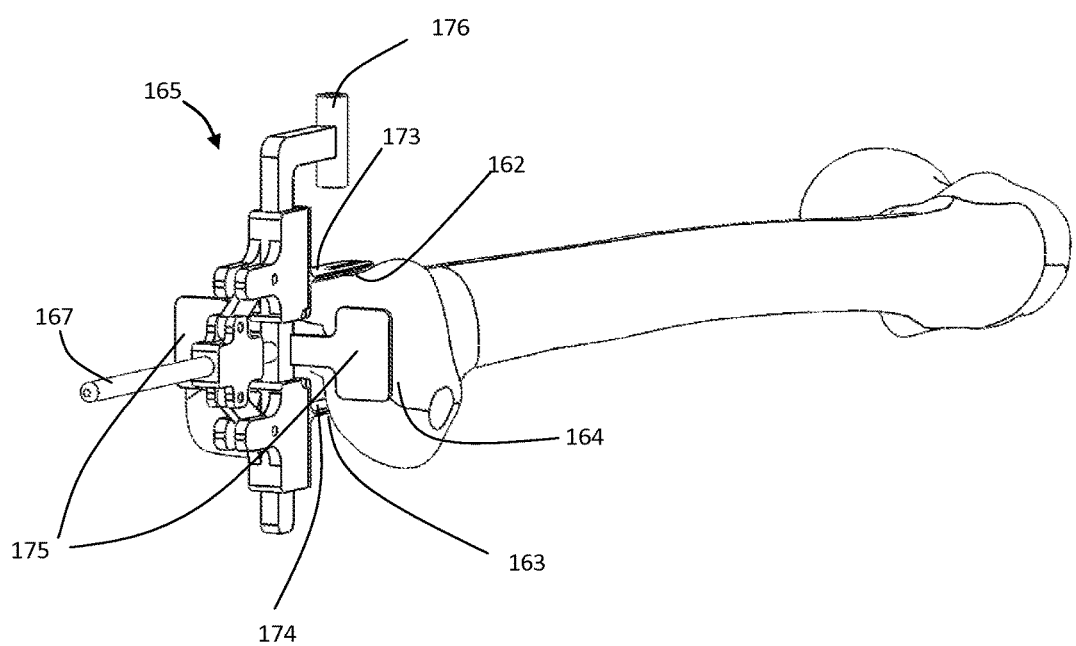
FIG. 28 is a perspective view of the knee center locator of FIG. 27 positioned relative to an end portion of a femur.

After the knee is exposed, the leg is placed in flexion and the knee center locator 165 is positioned as shown in FIG. 28. Anterior locating jaw 173 is placed in the deepest part of the trochlear groove 162, approximately in the middle of the trochlear groove 162, and posterior locating jaw 174 is placed in the deepest part of intercondylar notch 163, approximately in the middle of the intercondylar notch 163. Anterior locating jaw 173 and posterior locating jaw 174 are then pressed toward each other to clamp the distal femur in between them. Locating paddles 175 are then pressed against the distal surface of the condyles. The center of the knee will be located along the axis of PD guide bar 167, between 20 mm to 50 mm proximal to the locating paddles 175. Pin guide 176 is positioned perpendicular to the axis of PD guide bar 167 and between 20 mm to 50 mm from locating paddles 175. A pin can then be drilled into the distal femur along the axis of pin guide 176 to mark the location of the center of the knee.

Referring now to FIG. 5, once the center of the knee 56 is located, a pin device including a pin 30 and a generally spherical bead 31 is inserted into the anterior aspect of the distal femur, along the sagittal plane approximately perpendicular to the femoral anatomical axis and going through the center of the knee 56. The pin 30 is inserted so that the spherical bead 31 is at a predetermined distance (represented by the reference numeral 80) from the center of the knee 56. This position of bead 31 and the center of the femoral head 54 are two points used to define an axis 70' (otherwise referred to herein as the "approximate mechanical axis"), which extends from the center of the femoral head 54 to the center of bead 31, wherein benefits of defining such an axis 70' are discussed below.

The methods and devices of the present invention are used to locate an approximate mechanical axis 70', wherein this axis can be used in certain surgical approaches instead of using the "true" mechanical axis 70 of a femur. The reason for this is that the location of the center of the knee is inside the distal femoral bone and it cannot be directly accessed by typical physical access means. It is noted that while it is also possible to place the bead 31 in the coronal plane distal to the knee with the pin 30 approximately in line with the anatomical axis, such a placement may interfere with the proximal tibia when the knee is extended. In addition, it may be inconvenient to keep the knee flexed during the entire process of locating the mechanical axis. It should be noted that the approximation described here does not produce an error in locating the true mechanical axis when viewed in the coronal plane. In the sagittal plane, the angle between the true mechanical axis 70 and the approximate mechanical axis 70' can be compensated for using the length of the femur and the distance 80 between the spherical bead 31 and the center of the knee 56. Since femoral lengths vary from patient to patient, an average length can be assumed. It is estimated that for femoral lengths of 330 mm to 470 mm, the error can be about plus or minus one degree, for example.

Figure 6:
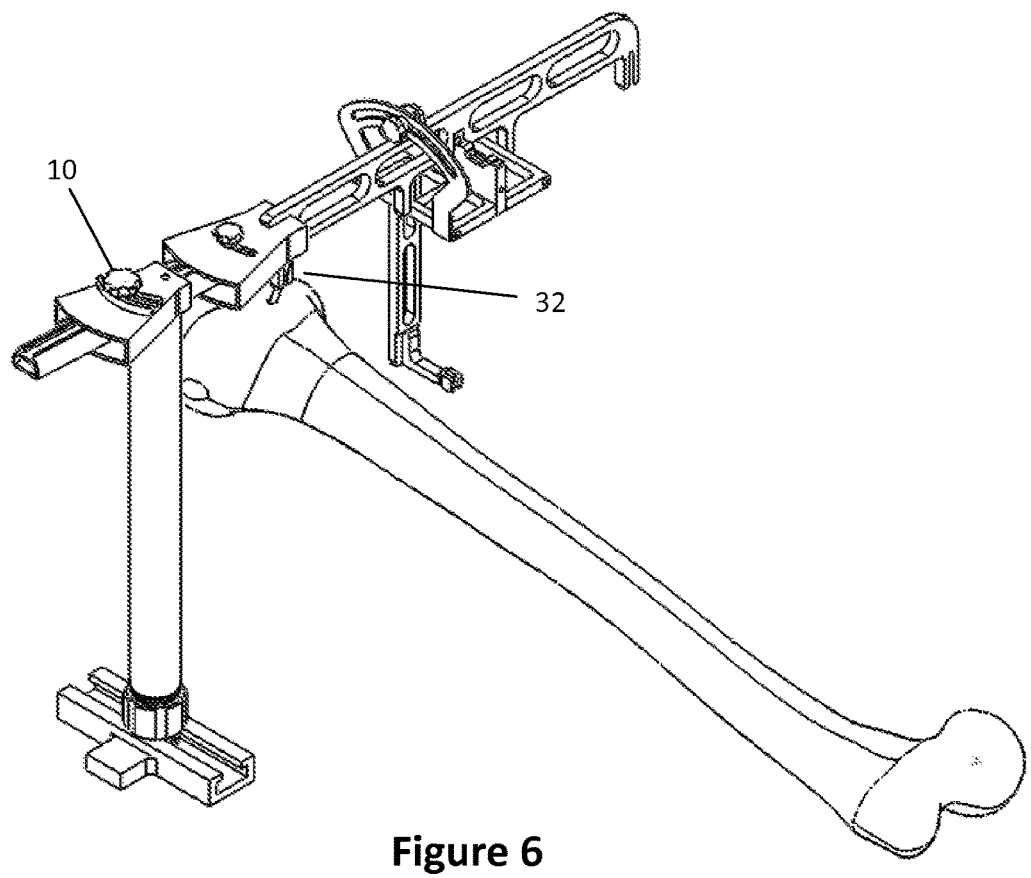
FIG. 6 is a perspective view of the mechanical axis finder of FIG. 2, with the femur engaged with a lateral locator slot via a pin.
Figure 7:
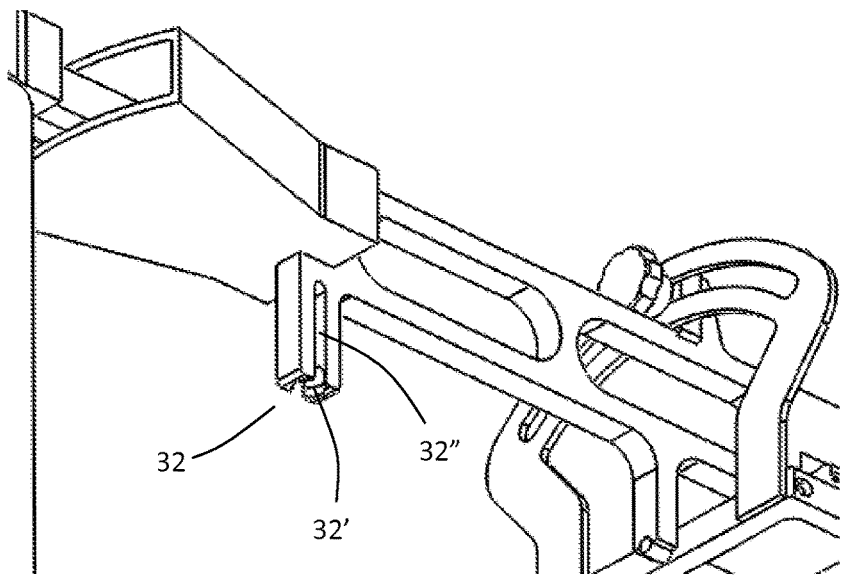
FIG. 7 is a bottom enlarged perspective view of the mechanical axis finder of the invention, which includes a view of a lateral locator slot.

After the pin 30 and bead 31 are located in a desired position relative to the center of the knee 56, the mechanical axis finder 1 is configured so that extension arm 3, swiveling arm 4, and locating arm 5 are aligned as shown in FIGS. 2 and 5, with base 2 positioned on the lateral aspect of the femur. Once the components are positioned in this way, locking screws 10, 16, and 21 are tightened. The knee is then swung laterally and manipulated so that bead 31 is captured inside a lateral locator slot 32 that extends downwardly from swiveling arm 4, wherein the slot 32 is best shown in FIG. 7 and the engagement between the slot 32 and the bead 31 is best shown in FIG. 6. It should be noted that when the knee is being moved to different locations, the femur will be pivoted about the center of the femoral head. To capture bead 31 inside lateral locator slot 32, locking screw 10 is loosened and extension arm 3 is adjusted translationally and rotationally while the knee is manipulated. When bead 31 is captured inside lateral locator slot 32, locking screw 10 is tightened to lock extension arm 3 in place. This position of lateral locator slot 32 marks the location represented by the first point 60 in FIG. 1.

Referring again to FIG. 7, a magnified view of a portion of mechanical axis finder 1 is illustrated, which includes a bottom perspective view of locator slot 32. Locator slot 32 includes a concave portion 32' that is capable of capturing bead 31 and a slot portion 32" that is capable of providing space for the cylindrical portion of pin 30 that extends beyond bead 31.

Swiveling arm 4 further includes a medial locator slot 33 (see FIGS. 3 and 8, for example), and locating arm 5 further includes a middle locator slot 34, wherein these configurations of the slots may be functionally and/or physically similar to that of locator slot 32. The purpose of locator slots 32, 33, and 34 is to identify the position of the center of bead 31 in space at certain points in the process of locating the femoral mechanical axis. Thus, when the position of locator slot 32, 33, or 34 is being referred to in the description of the present invention, it is to be understood that reference is being made to the center of the concave portion of the respective locator slot.

Figure 8:
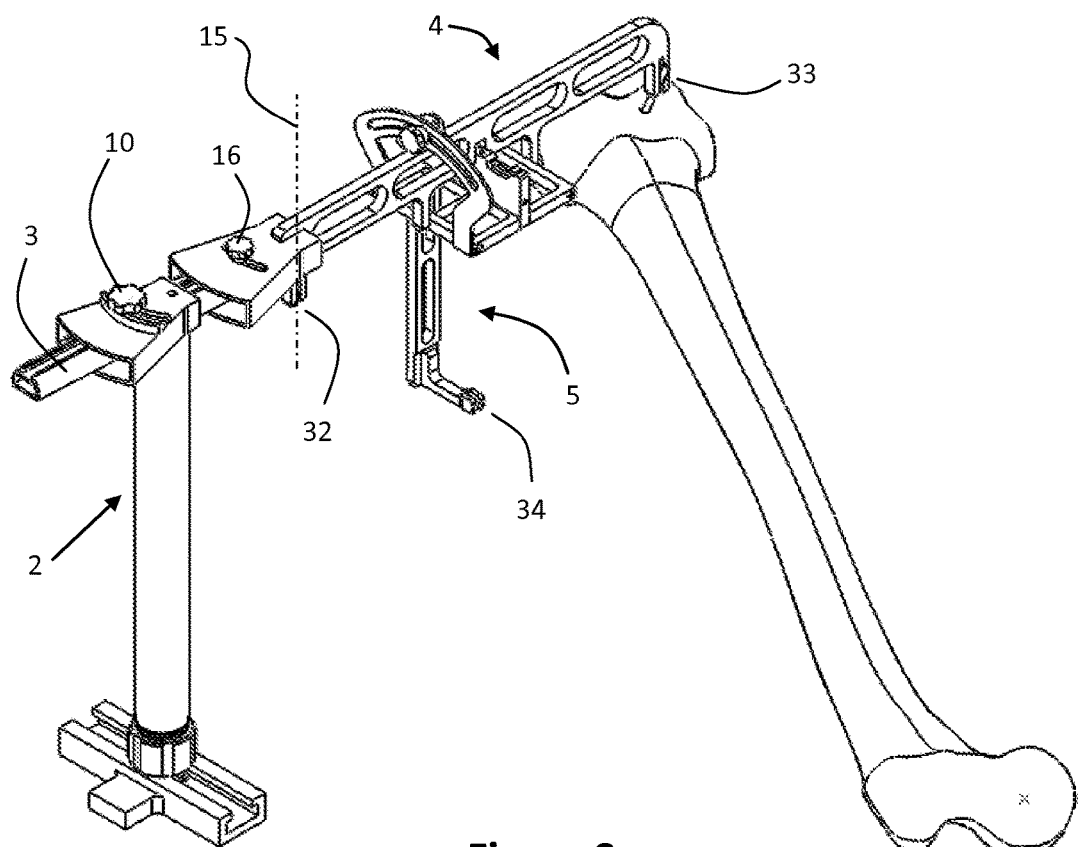
FIG. 8 is a perspective view of the mechanical axis finder of FIG. 2, with the femur engaged with a medial locator slot via a pin.

After first point 60 is identified by the process of capturing bead 31 inside the concave portion of lateral locator slot 32 and locking extension arm 3 in place by the tightening of locking screw 10, the bead 31 is removed from the lateral locator slot 32. The knee is then swung medially and manipulated in order for bead 31 to be captured next inside medial locator slot 33 of swiveling arm 4, as shown in FIG. 8. In order to accomplish this, locking screw 16 is loosened to adjust the position of swiveling arm 4 rotationally relative to extension arm 3. Locking screw 16 is tightened once bead 31 is captured inside medial locator slot 33. This position of medial locator slot 33 marks the location of second point 62 of FIG. 1. It can be seen that when swiveling arm 4 is rotated to capture bead 31, the position of lateral locator slot 32 does not change, since extension arm 3 is locked to base 2 and swiveling arm 4 is pivoted along axis 15, which goes through locator slot 32.

Figure 9:
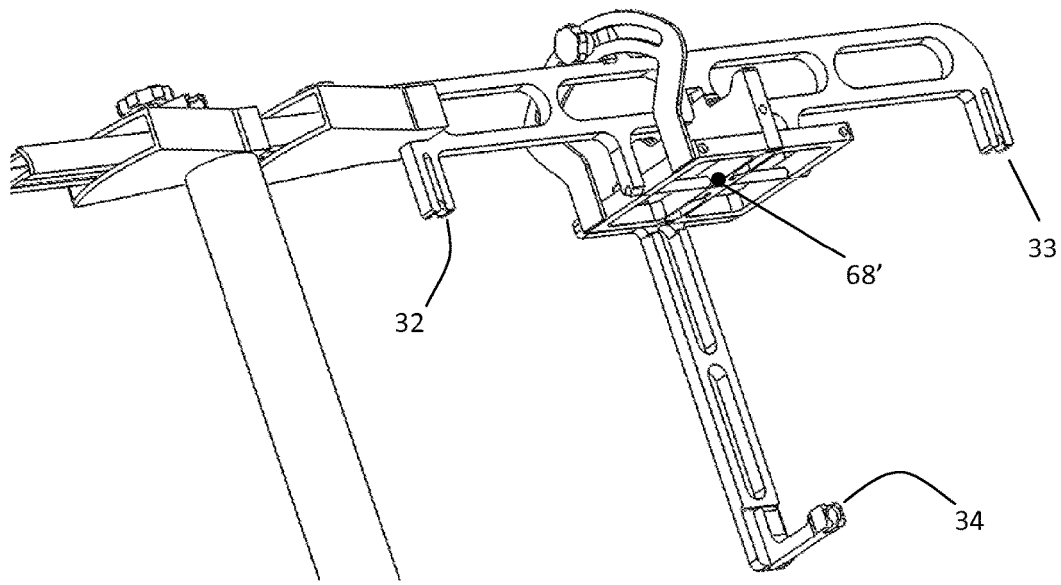
FIG. 9 is another perspective view of the mechanical axis finder of FIG. 2, which shows plural locator slots.

As is illustrated in FIG. 9, a point 68' can be defined along a line connecting lateral locating slot 32 and medial locator slot 33. Point 68' is positioned midway between the two points and corresponds to point 68 in FIG. 1, which is identified as the center of circle 66.

Figure 10:
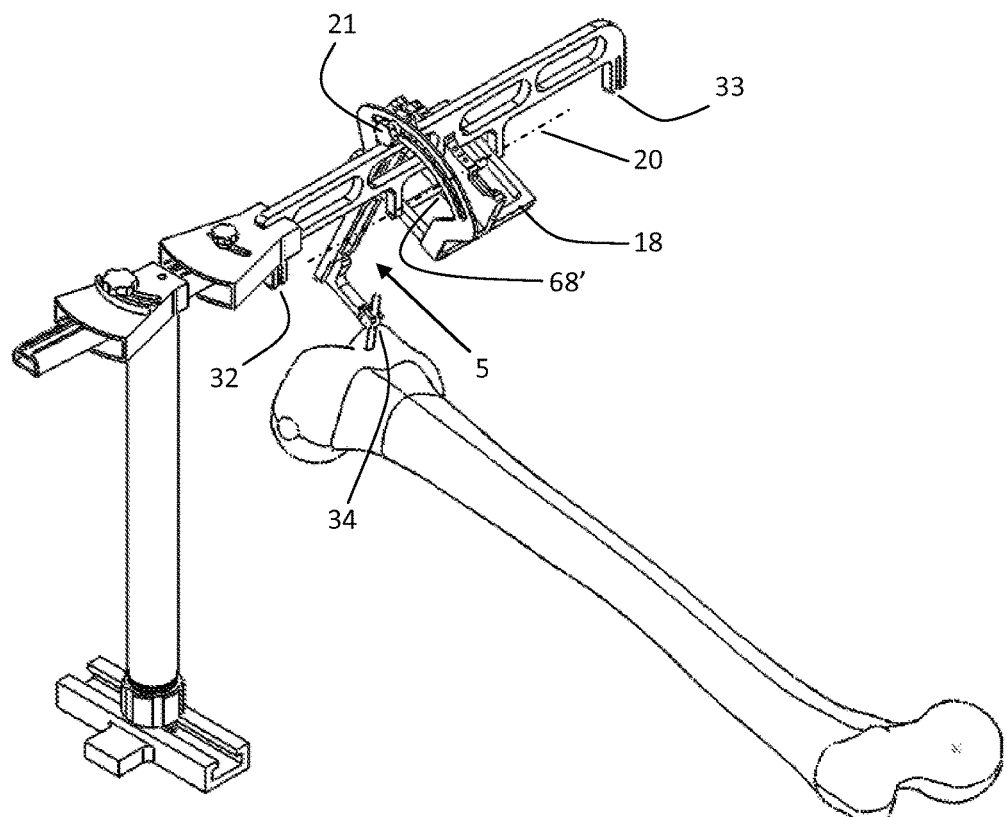
FIG. 10 is a perspective view of the mechanical axis finder of FIG. 2, with the femur engaged with a middle locator slot via a pin.

After bead 31 is captured inside the concave portion of medial locator slot 33 and swiveling arm 4 is rotationally locked relative to extension arm 3, the bead 31 is removed from the medial locator slot 33. The knee is then swung towards the posterior and lateral directions and manipulated such that bead 31 can be captured inside middle locator slot 34 of locating arm 5, as is shown in FIG. 10. In order to accomplish this, locking screw 21 is loosened to adjust the orientation of bracket 18 where locating arm 5 is attached. Locking screw 21 is tightened once bead 31 is captured inside middle locator slot 34. This position of middle locator slot 34 marks the location of third point 64 in FIG. 1. It can be seen that when bracket 18 is rotated, the positions of lateral locator slot 32, medial locator slot 33, and point 68' do not change. As locating arm 5 is adjusted to capture bead 31 inside middle locator slot 34, it rotates about axis 20, which goes through lateral locator slot 32, point 68', and medial locator slot 33. The distance from lateral locator 32 to point 68' is equal to the distance from medial locator 33 to point 68', and also equal to the distance from middle locator slot 34 to point 68'. Thus, lateral locator slot 32, medial locator slot 33, and middle locator slot 34 identify points on a circle having its center at 68', and the line from middle locator slot 34 to point 68' is perpendicular to the line from lateral locator slot 32 to medial locator slot 33. Furthermore, the line from middle locator slot 34 to point 68' is perpendicular to axis 72 of FIG. 1.

Figure 11:
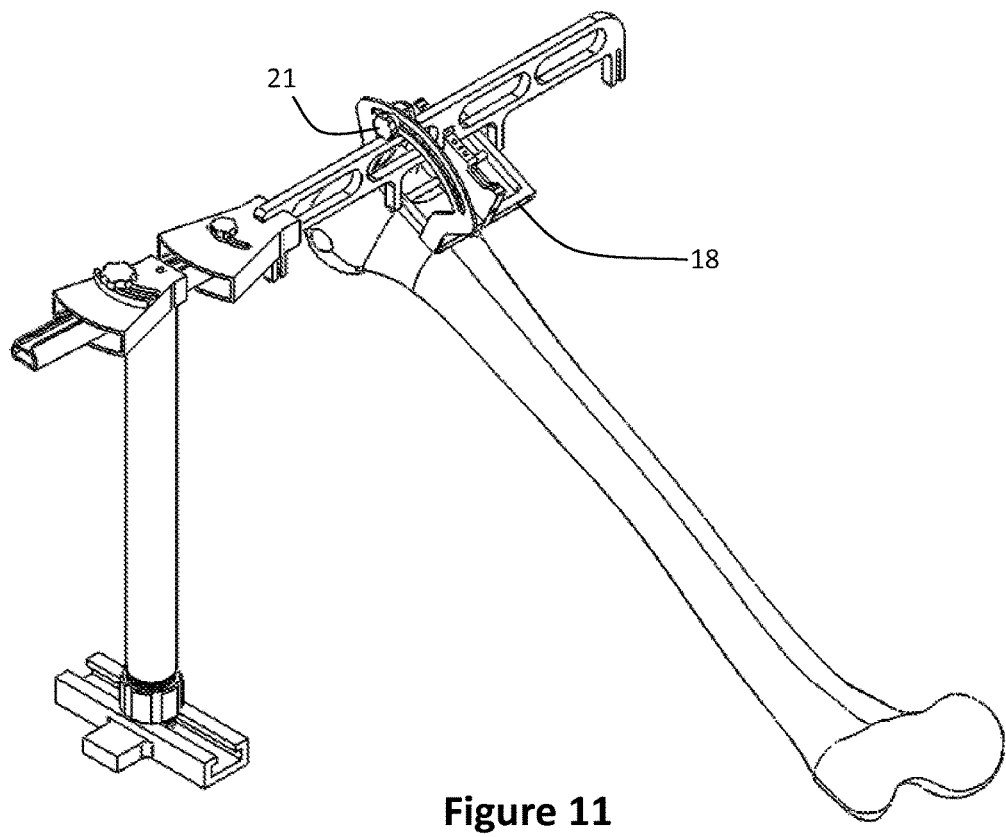
FIG. 11 is a perspective view of the mechanical axis finder of FIG. 2, with the femur engaged with a final locator slot via a pin.
Figure 12:
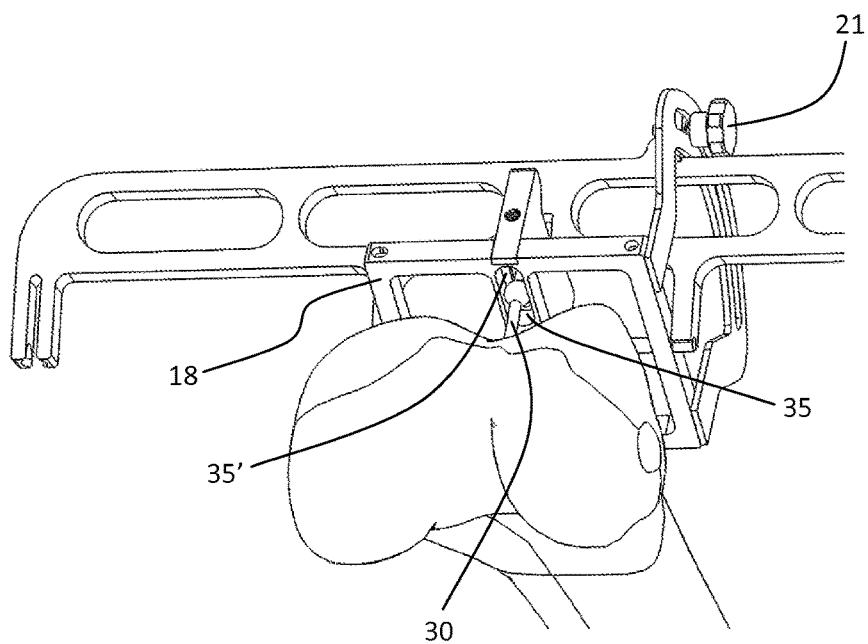
FIG. 12 is an enlarged bottom perspective view of a portion of the mechanical axis finder of FIG. 2, including the final locator slot.

Locating arm 5 is then removed from bracket 18 and bead 31 is placed inside a final locator slot 35 of bracket 18, as shown in FIGS. 11 and 12. Final locator slot 35 has a shoulder 35', as shown in FIG. 12. When bead 31 is placed inside slot 35, it abuts against shoulder 35' such that the line from point 68' to bead 31 is perpendicular to the line from middle locator slot 34 to point 68'. Thus, when bead 31 is placed inside final locator slot 35, bead 31 becomes aligned with axis 72 of FIG. 1.

Figure 13:
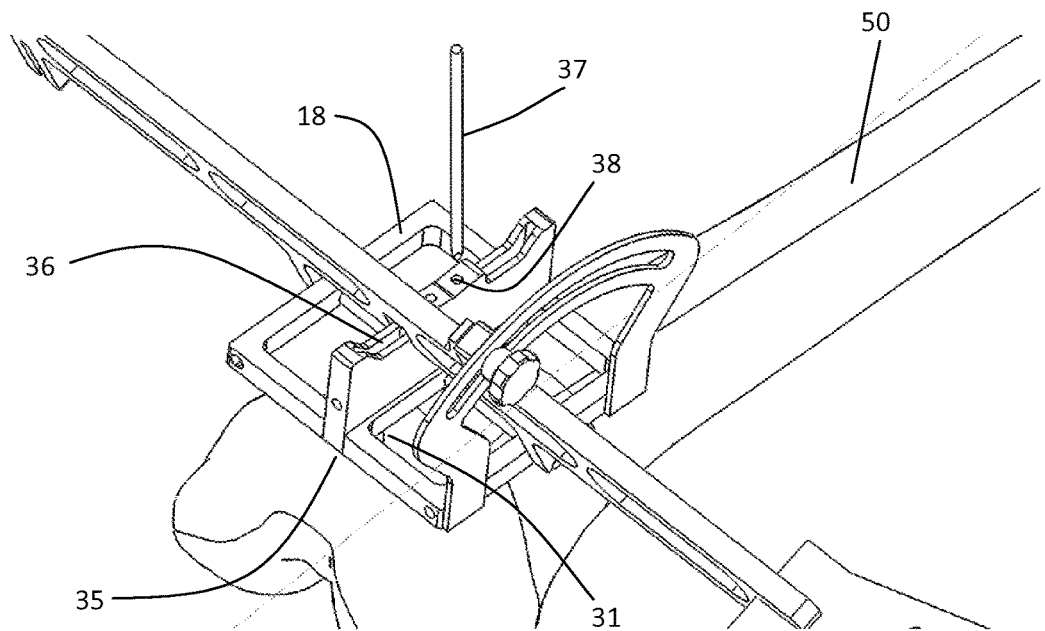
FIG. 13 is an enlarged top perspective view of the mechanical axis finder of FIG. 2, which shows the top portion of a bracket.

FIG. 13 shows a top perspective view that includes bracket 18 positioned relative to femur 50. When bead 31 is positioned inside final locator slot 35, the top cylindrical portion of pin 30 is captured inside guide slot 36. This constrains the femur to be oriented such that the center of the knee is coplanar with the middle plane of guide slot 36. The femur is then held in this position while guide pin 37 is drilled into femur 50 through guide hole 38, which is spaced from guide slot 36. Guide hole 38 is angled from the line connecting point 68' and bead 31 in such a way that it compensates for the angle between the true mechanical axis 70 and the approximate mechanical axis 70'. Thus, when pin 37 is drilled into femur 50, it is perpendicular to axis 70 of FIG. 1.

Figure 14:
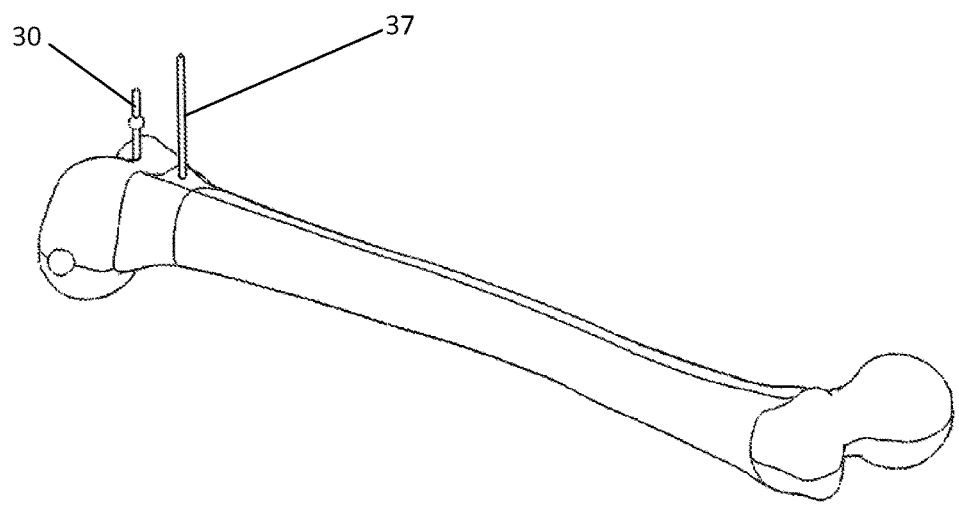
FIG. 14 is a perspective view of guide pins positioned in representative locations in a femur.
Figure 15:
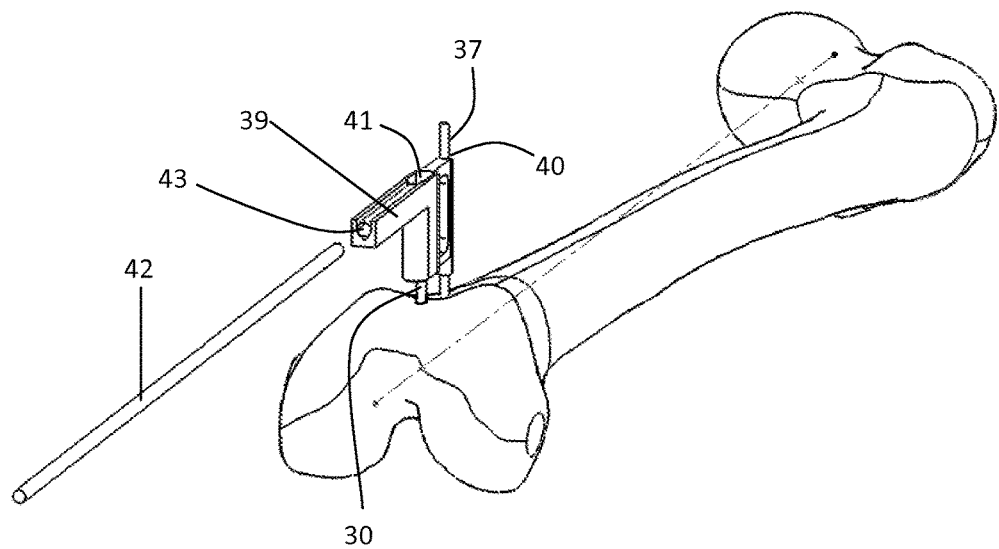
FIG. 15 is a perspective view of an alignment guide positioned relative to a femur.
Figure 16:
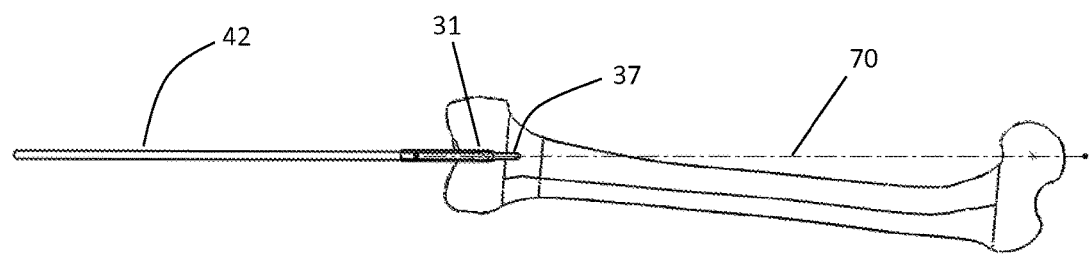
FIG. 16 is a top view of a femur with an alignment rod positioned in line with the mechanical axis when viewed in the coronal plane.
Figure 17:
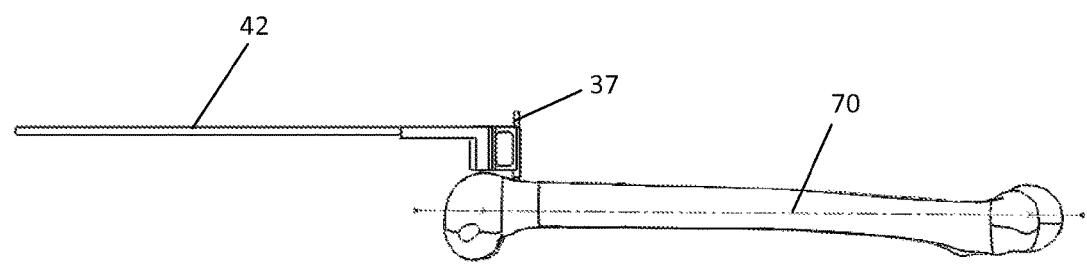
FIG. 17 is a side view of a femur with an alignment rod positioned parallel to the mechanical axis when viewed in the sagittal plane.

The mechanical axis finder 1 is then removed from the patient while leaving guide pins 30 and 37 positioned in their respective locations in the femur 50, as shown in FIG. 14. A rod alignment guide 39 is then placed over pins 30 and 37, as shown in FIG. 15. In particular, rod alignment guide 39 includes a guide hole 40 and guide slot 41, wherein guide hole 40 is slideable over pin 37 and guide slot 41 is slideable over bead 31 of pin 30. Finally, an alignment rod 42 is placed inside a guide hole 43 of alignment guide 39. Alignment rod 42 will be collinear with the mechanical axis 70 when viewed in the coronal plane and parallel to the mechanical axis 70 when viewed in the sagittal plane, as shown in FIGS. 16 and 17. Guide pin 37 will be perpendicular to the mechanical axis 70 when viewed in the sagittal plane. The line connecting the center of bead 31 and the axis of guide pin 37 will be collinear with the mechanical axis when viewed in the coronal plane.

Referring now to FIGS. 18-20, an embodiment of a mechanical axis finder 101 of the invention is illustrated, which generally includes a base 102, an extension arm 103, a swiveling arm 104, and a locating attachment 105. Base 102 includes a post 107 and a locking clamp 107" attached to a split end 107'. Extension tube 106' extends from arm clamp 106, and can slide vertically and rotatably relative to post 107. When locking clamp 107" is locked, split end 107' is compressed, locking extension arm clamp 106 to post 107. In general, clamp 106 includes a base or structure that allows extension arm 103 to translate and rotate when in an unlocked configuration. However, when clamp 107" and clamp 106 are both in a locked configuration, extension arm 103 is not translatable or rotatable relative to base 102.

Arm clamp 106 includes a sliding member 108 and a locking nut 109. Sliding member 108 further includes a pivot peg 110 and threaded stud 111. Sliding member 108 is designed to slide within a longitudinal slot 112 of extension arm 103. Pivot peg 110 pivots inside hole 113 of clamp 106 while threaded stud 111 slides within or along curved slot 114 and engages with locking nut 109. In this way, when clamp 106 is in an unlocked configuration, extension arm 103 is translatable relative to clamp 106 (via slot 112) and is rotatable at the same time about pivot peg 110. The components of clamp 106 are therefore moveable to their desired locations relative to each other when in the unlocked configuration, and then the locking nut 109 can be tightened, such as by turning the locking nut 109 until it locks extension arm 103 to clamp 106. When clamp 107" is locked, the extension arm 103 will be fixed translationally and rotationally relative to base 102.

Extension arm 103 is also connected to pivoting clamp 115 of swiveling arm 104 through a pin (not visible in the figures) that allows swiveling arm 104 to rotate relative to extension arm 103 along axis 116. A locking screw 117 is threaded into a matching threaded hole in extension arm 103 through a curved slot 118 in pivoting clamp 115. When in an unlocked configuration, the extension arm 103 and swiveling arm 104 will be moveable relative to each other, and then when the locking screw 117 is tightened, it locks swiveling arm 104 to extension arm 103.

A bracket 119 is connected to the swiveling arm 104 so that bracket 119 can rotate relative to swiveling arm 104. Bracket 119 has a sliding member 120 and an arch 121 that extends upwardly from one side of bracket 119, which arch 121 includes a curved slot 122. A locking screw 123 is threaded into a threaded hole of swiveling arm 104, and is slidable along curved slot 122 of arch 121. When locking screw 123 is tightened, it locks the bracket 119 in place relative to swiveling arm 104. Locating arm 105 is also removably attached to bracket 119, wherein locating arm 105 is lockable via a locking screw 124.

The mechanical axis finder 101 further includes a number of mechanisms for locating certain points during the process of locating the mechanical axis of the femur. In particular, swiveling arm 104 includes a lateral locator member 132 and a medial locator member 133, and locating attachment 105 includes a middle locator member 134. Locator members 132, 133, and 134 each include an extending finger 152, 153, 154, respectively, wherein such fingers can extend at an approximately perpendicular angle relative to their respective locator members and can either be fixed or moveable relative to their respective locator members.

In an exemplary method of using mechanical axis finder 101, an incision is first made to expose the knee joint of a patient. After the knee joint is exposed, the center of the knee is identified by the surgeon in the coronal and sagittal planes. The center of the knee may be found by using a knee center locator system or device similar to that described herein, or by using another method and/or device. In accordance with an aspect of the invention, a pin 130 with a marking or band 131 (shown in FIG. 22, for example) is inserted into the anterior aspect of the distal femur, along the sagittal plane and going through the center of the knee. The pin 130 is inserted such that band 131 is at a predetermined distance from the center of the knee. This position of band 131 defines an axis (otherwise referred to herein as the "approximate mechanical axis"), which extends from the center of the femoral head to the center of band 131.

Instead of locating the "true" mechanical axis of a femur, the present invention provides for methods and devices to locate an approximate mechanical axis. The reason for this is that the location of the center of the knee is inside the distal femoral bone and it cannot be directly accessed by typical physical access means. It is noted that while it is also possible to place the band 131 in the coronal plane distal to the knee with the pin 130 approximately in line with the anatomical axis, such a placement may interfere with the proximal tibia when the knee is extended. It may be inconvenient to keep the knee flexed during the entire process of locating the mechanical axis. It should be noted that the approximation described does not produce an error in locating the true mechanical axis when viewed in the coronal plane. In the sagittal plane, the angle between the true mechanical axis and the approximate mechanical axis can be compensated for given the length of the femur and the distance between the band 131 and the center of the knee. Since femoral lengths vary from patient to patient, an average length can be assumed. It is estimated that for femoral lengths of 330 mm to 470 mm, the error can be about plus or minus one degree, for example.

Figure 21:
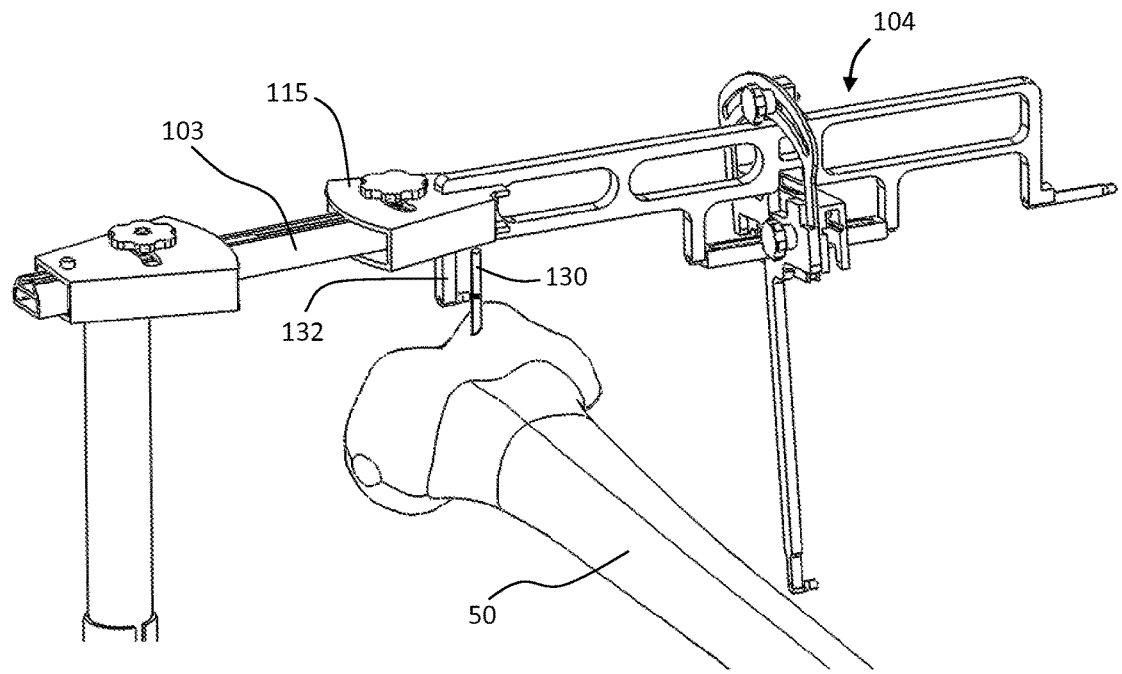
FIG. 21 is a perspective view of the mechanical axis finder with a femur engaged with a lateral locator member.
Figure 22:
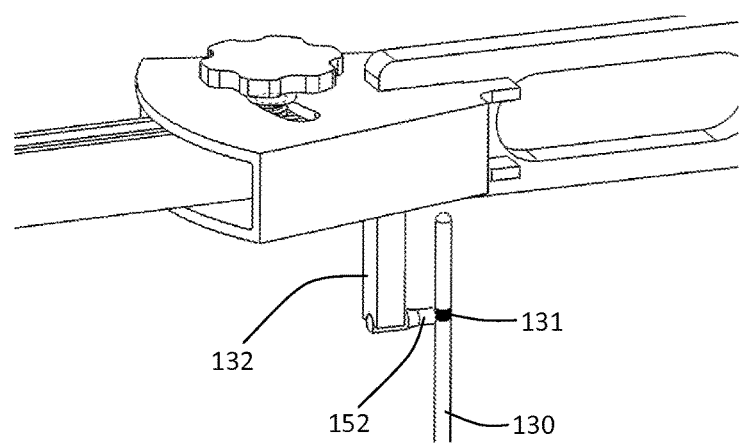
FIG. 22 is an enlarged perspective view of a portion of the mechanical axis finder of FIG. 20, illustrating the alignment of a pin with the lateral locator member.

Initially, the mechanical axis finder 101 is adjusted such that extension arm 103, swiveling arm 104, and locating arm 105 are aligned with each other. The vertical position of extension arm clamp 106 may also be adjusted to provide space for the knee to be moved about during the process of locating the femoral mechanical axis. Once the components are positioned in this way, clamp 107", locking nut 109, and locking screws 117 and 123 are tightened. The knee is then swung laterally and manipulated so that band 131 is lined up with finger 152 of locator member 132 and contacts the tip of finger 152, as shown in FIGS. 21 and 22. It should be noted that when the knee is swung around, the femur will be pivoted about the center of the femoral head. To position band 131 in this manner, locking nut 109 is loosened and extension arm 103 is adjusted translationally and rotationally while the knee is manipulated. When band 131 is lined up and is in contact with finger 152, locking nut 109 is tightened to lock extension arm 103 in place. This position of band 131 is generally the location represented by the first point 60 in FIG. 1.

The purpose of locator members 132, 133, and 134 is to determine the position of the band 131 in space at certain points in the process of locating the femoral axis. Thus, when the position of locator members 132, 133, or 134 is being referred herein, it is understood that what is being referred to is the point along the axis of the finger of the locator member and offset from the tip of the finger such that when the band 131 is aligned with the finger and in contact with the tip of the finger, the point is coincident with the center of band 131.

After band 131 is positioned so that it is aligned with and in contact with finger 152 and extension arm 103 is locked in place by the tightening of locking nut 109, the knee is then swung medially and manipulated in order for band 131 to be aligned with and in contact with finger 153 of medial locator member 133. In order to accomplish this, locking screw 117 is loosened to adjust the position of swiveling arm 104 rotationally relative to extension arm 103. Locking screw 117 is tightened once band 131 is positioned relative to medial locator member 133, as described above. This position of medial locator member 133 marks the location of second point 62 of FIG. 1. It can be seen that when swiveling arm 104 is rotated into position relative to band 131, the position of lateral locator member 132 does not change since extension arm 103 is locked to base 102. A point 168 can be defined along the line connecting locator member 132 and locator member 133. Point 168 is located midway between the two locator members and corresponds generally to point 68 in FIG. 1.

Figure 23:
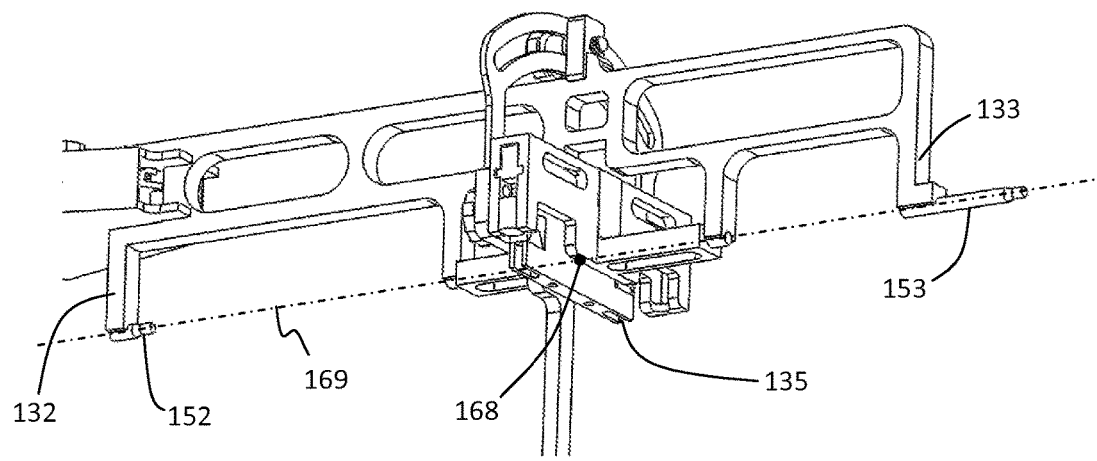
FIG. 23 is a bottom perspective view of the mechanical axis finder of FIG. 18.

After band 131 is positioned so that it is aligned with and in contact with finger 153 and swiveling arm 104 is rotationally locked relative to extension arm 103, the knee is then swung towards the posterior and lateral directions and manipulated such that band 131 is aligned with and in contact with finger 154 of middle locator member 134. In order to accomplish this, locking screw 123 is loosened to adjust the orientation of bracket 119 where locating arm 105 is attached. Locking screw 123 is tightened once band 131 is properly positioned relative to middle locator member 134. This position of middle locator member 134 marks the location of third point 64 in FIG. 1. It can be seen that when bracket 119 is rotated, the positions of lateral locator member 132, medial locator member 133, and point 168 of FIG. 23 do not change. As locating arm 105 is adjusted to position band 131 relative to middle locator member 134, it rotates about an axis 169 that extends through lateral locator member 132, point 168, and medial locator member 133. The distance from lateral locator member 132 to point 168 is equal to the distance from medial locator member 133 to point 168, and also equal to the distance from middle locator member 134 to point 168. Thus, lateral locator member 132, medial locator member 133, and middle locator member 134 identify points on a circle with center at point 168, and the line from middle locator member 134 to point 168 is perpendicular to the line from lateral locator member 132 to medial locator member 133.

Figure 24:
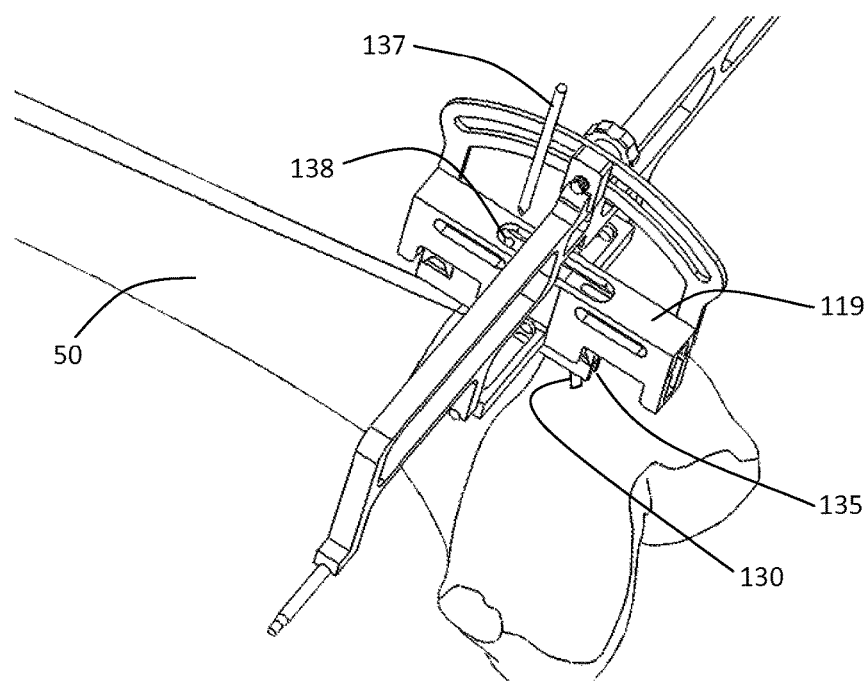
FIG. 24 is a top perspective view of the mechanical axis finder of FIG. 18 relative to a portion of a femur.
Figure 25:
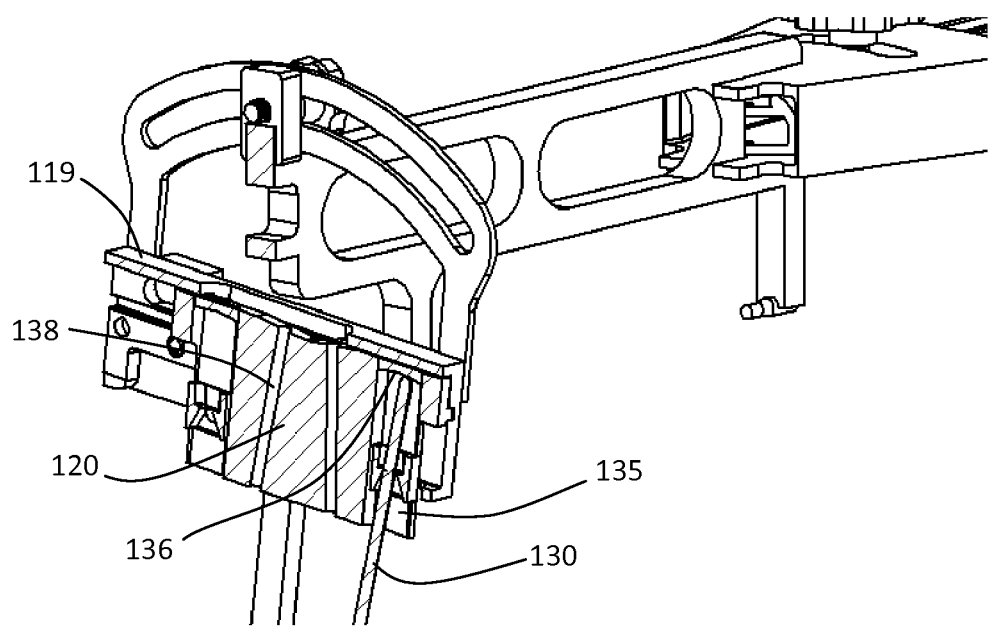
FIG. 25 is a perspective view of a portion of a mechanical axis finder, with a portion of a bracket thereof shown in cross-section.

Locating arm 105 is then removed from bracket 119 and pin 130 is placed inside a final locator slot 135 of sliding member 120 of bracket 119, as shown in FIG. 24. FIG. 25 includes a cross-sectional view of bracket 119, which shows final locator slot 135 with a stopper end 136. Stopper end 136 is designed such that when the top end of pin 130 abuts against it, the line from point 168 to band 131 is perpendicular to the line from middle locator slot 134 to point 168. Thus, when pin 130 is placed inside final locator slot 135, band 131 becomes aligned with axis 72 (shown in FIG. 1).

As shown in FIG. 24, when pin 130 is positioned inside final locator slot 135, the femur is constrained to be oriented such that the center of the knee is coplanar with the middle plane of final locator slot 135. The femur is then held in this position while guide pin 137 is drilled into femur 50 through guide hole 138, which is spaced from final locator slot 135.

Guide hole 138 is angled from the line connecting point 168 and band 131 in such a way that it compensates for the angle between the true mechanical axis 70 and the approximate mechanical axis 70'. Thus, when pin 137 is drilled into femur 50, it is perpendicular to axis 70.

The mechanical axis finder 101 is then removed from the patient while leaving guide pins 130 and 137 positioned in their respective locations in the femur in a similar manner to that shown in FIG. 14 relative to guide pins 30 and 37. A rod alignment guide can then be placed over pins 130 and 137. In particular, the rod alignment guide can include a guide hole, wherein the guide hole is slideable over pin 137 and a guide slot, wherein the guide slot is slideable over pin 130. Finally, an alignment rod can be placed inside another guide hole of the alignment guide. The alignment rod will be collinear with the mechanical axis when viewed in the coronal plane and parallel to the mechanical axis when viewed in the sagittal plane. Guide pin 137 will be perpendicular to the mechanical axis when viewed in the sagittal plane. The line connecting the center of band 131 and the axis of guide pin 137 will be collinear with the mechanical axis when viewed in the coronal plane.

The present invention has now been described with reference to several embodiments thereof. The entire disclosure of any patent or patent application identified herein is hereby incorporated by reference. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the structures described herein, but only by the structures described by the language of the claims and the equivalents of those structures.

The invention claimed is:

1. An instrument for locating a femoral mechanical axis by identifying the locations of at least three points in space in relation to the center of a femoral head, the at least three points in space being on a circle, the circle lying on a plane and being on a sphere whose center coincides with the center of the femoral head, and the plane of the circle being not coincident with the center of the femoral head, wherein the instrument comprises:
   a base member comprising a post and an extension arm clamp attached to a first end of the post;
   an extension arm that is at least one of translationally and pivotally attached to the extension arm clamp of the base member;
   a swiveling arm pivotally attached to a first end of the extension arm, the swiveling arm comprising a lateral locator member at a swiveling arm first end and that is positionable for identifying a first of the at least three points and a medial locator member at a swiveling arm second end that is positionable for identifying a second of the at least three points;
   a bracket pivotally attached to the swiveling arm; and
   a locating arm removably attached to the bracket, the locating arm comprising a middle locator member that is positionable for identifying the third of the at least three points,
   wherein a representative axis perpendicular to the plane containing the circle and passing through the center of the circle is collinear with the femoral mechanical axis after the femur is moved about the center of the femoral head such that a center of a knee coincides with the representative axis.

2. The instrument of claim 1, wherein the swiveling arm is pivotable relative to the extension arm in a direction that is generally parallel to a direction in which the extension arm is pivotable relative to the post.

3. The instrument of claim 1, wherein the bracket is pivotable relative to the swiveling arm in a direction that is generally perpendicular to a direction in which the swiveling arm pivots relative to the extension arm.

4. The instrument of claim 1, wherein each of the extension arm clamp, the extension arm, the swiveling arm, and the bracket are lockable and unlockable relative to the base member, the extension arm clamp, the extension arm, and the swiveling arm, respectively.

5. The instrument of claim 1, wherein the bracket comprises a base portion from which an arch portion extends, wherein the arch portion comprises a curved slot along which a locking screw of the swiveling arm is slideable.

6. The instrument of claim 1, in combination with at least one locating pin that is positionable within a femur in a predetermined relationship with a center of the knee.

7. The combination of claim 6, wherein the at least one locating pin is positionable within an anterior aspect of a distal femur, along a sagittal plane approximately perpendicular to the femoral anatomical axis, and into the center of the knee.

8. The combination of claim 6, wherein the at least one locating pin comprises a bead member for cooperative engagement with at least one of the lateral locator member, the medial locator member, and the middle locator member.

9. The combination of claim 8, wherein at least one of the lateral locator member, the medial locator member, and the middle locator member comprises a structure comprising an inner slot.

10. The combination of claim 6, wherein the at least one locating pin comprises a band for cooperative engagement with at least one of the lateral locator member, the medial locator member, and the middle locator member.

11. The combination of claim 10, wherein at least one of the lateral locator member, the medial locator member, and the middle locator member comprises an elongated member with a distal tip.

12. The combination of claim 6, further comprising an alignment guide positionable over at least a portion of the at least one locating pin.

13. The combination of claim 12, further comprising an alignment rod engageable with an aperture of the alignment guide for identifying the location and direction of the femoral mechanical axis.

14. A method of locating a femoral mechanical axis comprising:
identifying a representative sphere traced by a trace point offset by a predetermined distance from a center of a knee, wherein a center of the representative sphere is coincident with a center of a femoral head;
identifying at least three points on the representative sphere;
locating the center of a circle defined by the at least three points on the representative sphere;
identifying a line passing through the center of, and perpendicular to the plane of, the circle defined by the at least three points on the representative sphere;
positioning the femur such that a line connecting the center of the femoral head and the trace point is coincident with the line passing through the center of, and perpendicular to the plane of, the circle defined by the at least three points on the representative sphere; and
placing a plurality of locating devices on the femur to identify the location of the femoral mechanical axis in both the coronal and sagittal planes, such locating devices being positioned on the femur in such a way as to compensate for the predetermined offset of the trace point from the center of the knee so that the line connecting the center of the femoral head and the trace point has a predetermined angular offset from the femoral mechanical axis;
wherein the at least three points of the representative sphere are identified using an instrument comprising:
a base member;
an extension arm clamp translationally and pivotally attached to the base member;
an extension arm translationally and pivotally attached to the extension arm clamp;
a swiveling arm pivotally attached to a distal first end of the extension arm, the swiveling arm comprising a lateral locator member at a proximal swiveling arm first end for identifying a first of the at least three points and a medial locator member at a distal swiveling arm second end for identifying a second of the at least three points;
a bracket pivotally attached to the swiveling arm; and
a locating arm removably attached to the bracket, the locating arm comprising a middle locator member for identifying the third of the at least three points.

15. The method of claim 14, wherein the plurality of locating devices comprises at least one of a pin and a marker.

16. The method of claim 15, wherein the step of identifying at least three points on the representative sphere comprises positioning at least one locating pin within a femur so that a portion of the pin is located at the predetermined distance from the center of the knee.

17. The method of claim 16, wherein the instrument further comprises an alignment guide positionable over at least a portion of the at least one locating pin.

* * * * *